United States Patent [19]

Levine

[11] Patent Number: 4,476,857

[45] Date of Patent: Oct. 16, 1984

[54] ARM SUPPORT

[76] Inventor: Norman D. Levine, 2205 NW. 30th Pl., Pompano Beach, Fla. 33060

[21] Appl. No.: 458,035

[22] Filed: Jan. 14, 1983

[51] Int. Cl.³ .......................................... A61F 13/00
[52] U.S. Cl. .................................... 128/77; 128/165; 273/189 A
[58] Field of Search .................... 128/87 R, 157, 165, 128/80 R, 77, 89 R; 273/189 R, 189 A

[56] References Cited

U.S. PATENT DOCUMENTS

| | | | |
|---|---|---|---|
| 4,014,327 | 3/1977 | Spiro | 128/165 |
| 4,084,586 | 4/1978 | Hettick | 128/157 |
| 4,128,097 | 12/1978 | Bilinsky et al. | 128/165 |

*Primary Examiner*—John D. Yasko
*Attorney, Agent, or Firm*—Malin, Haley, McHale

[57] ABSTRACT

A therapeutic arm support including a full-length, preferably, nylon covered neoprene sleeve, an upper and a lower elastic strip or closure each attached adjacent a different end of the sleeve, and a removable substantially rigid splint installable between the upper and lower closures or bands. The sleeve is a tapered tubular shape to mate generally over the forearm of the user substantially covering the forearm from just above the wrist to just below the elbow. The neoprene sleeve includes nylon or the like covering on either side for added strength and to aid in installing the sleeve over the forearm. Suitably sized, the sleeve provides pressure over the entire forearm from the stretched neoprene/nylon layer. In addition to compression, the sleeve absorbs and retains body heat, providing therapeutic heat retention for healing use. The upper and lower elastic closures are adjustable in installation tension to provide both direct added compression to the damaged forearm muscles and tendons and along the mid-portion to provide upper wrist control. The splint may be curved or bent to provide added pressure along the mid-portion of the forearm.

5 Claims, 2 Drawing Figures

ARM SUPPORT

BACKGROUND OF THE INVENTION

This invention relates generally to orthopedic splints and more particularly to the field of such splints used by tennis players and others suffering from tennis elbow or those who wish to prevent developing this ailment while playing tennis or more generally involved in repeated pressure on the wrist and forearm tendons.

Presently, someone suffering from epicondylitis, commonly known as "tennis elbow" and/or analytis, tendonytis or the like, may treat the affliction by refraining from strenuous exercise of those torn muscles and allowing the ligiments that join the forearm radius and ulna to the two epicondylis on the end of the upper arm bone to rest and heal. Certain medications may expedite the healing and/or reduce the person's discomfort.

Another alternative for those wishing to remain active is to wrap the forearm with a elastic band to support the torn muscles and inflamed ligaments. However, in addition to being ineffective in helping a person with inflamed muscles, the elastic bands presently available restrict smooth arm movement e.g. during tennis play.

In addition to an elastic band, various patented devices, all having one or more shortcomings, may be found in prior art. Two early devices used in golfing are intended only to help stiffen the golfer's entire arm to improve his game. These are disclosed in U.S. Pat. Nos. 1,414,012 and 2,809,042. No therapeutic benefits are therein disclosed or claimed.

Two U.S. Pat. Nos. 3,693,973 and 4,014,327, are specifically intended for use in playing tennis. However, U.S. Pat. No. 3,693,973 is intended as only a tennis stroke training device attachable to the user's forearm then rigidly interengagable to the handle of a tennis racket. U.S. Pat. No. 4,014,327 discloses a tennis elbow split having a pair of spaced apart arm bands held thusly by a rigid member held in a flexible pocket or cover. The rigid member is also intended to press slightly against the inside of the forearm.

To replace previously discussed elastic bands, U.S. Pat. No. 3,877,426 teaches a muscle support intended to be worn e.g. around the user's forearm to create pressure on the muscles therein. This support is specifically curved to mate over the varying circumferences of a forearm. No rigidity or longitudinal support is provided over a length over the entire forearm.

The present invention provides pressure over a substantial portion of the forearm, therapeutic warmth over this same area by conserving body heat, localized additional adjustable pressure or compression of the most painful, damaged area of the upper forearm, additional adjustable upper wrist support, absorption of a portion of the shock input to the arm during further tennis playing or other such strenuous arm activity, and a removable rigid splint for maximum stability and forearm control. The rigid splint also prevents over-rotation of the lower arm and slight additional forearm muscle pressure midway along the forearm.

BRIEF DESCRIPTION OF THE INVENTION

A therapeutic arm support including a full-length, preferrably, nylon covered neoprene sleeve, an upper and a lower elastic strip or closure each attached adjacent a different end of the sleeve, and a removable substantially rigid splint installable between the upper and lower closures. The sleeve is a tapered tubular shape to mate generally over the forearms of the user substantially covering the forearm just above the wrist to just below the elbow. The neoprene sleeve includes nylon or the like covering on either side for added strength and to aid in installing the sleeve over the forearm. Suitably sized, the sleeve provides pressure over the entire forearm from the stretched neoprene/nylon layer. In addition to compression, the sleeve absorbs and retains body heat, providing therapeutic heat retention for healing use. The upper and lower elastic closures are adjustable in installation tension to provide both direct added compression to the damaged forearm muscles and tendons and to provide upper wrist control. The splint may be curved or bent along the mid-portion to provide added pressure along the mid-portion of the forearm.

It is therefore an object of this invention to provide an arm support which provides therapeutic compressive support over substantially the entire forearm.

It is another object of this invention to provide an arm support having a neoprene sleeve which provides therapeutic body heat absorption and/or retention over substantially the entire forearm.

It is still another object of this invention to provide the above arm support having an elastic band attached at one end adjacent the upper and the lower end of the arm support sleeve, each elastic band for providing additional adjustable arm compression.

And still another object of this invention to provide a removable substantially rigid splint which may be optionally installed between the above elastic bands for increased stability and forearm control.

And yet another object of this invention is to absorb at least a portion of the shock input to the arm caused by further tennis playing or other strenuous arm activity.

In accordance with these and other objects which will be apparent hereinafter, the instant invention will now be described with particular reference to the accompanying drawings.

PREFERRED EMBODIMENT OF THE INVENTION

Figure 1:
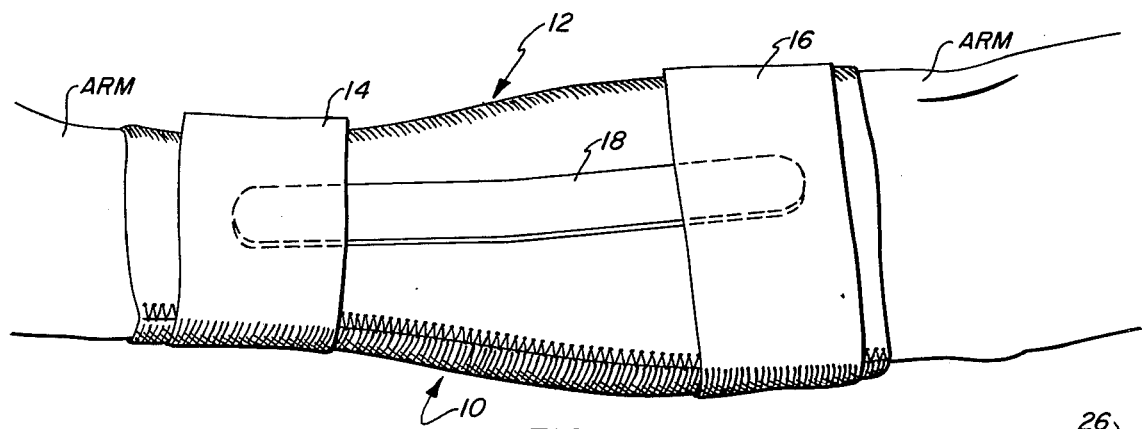
FIG. 1 is a side elevation view of the invention, including optional splint, applied to a user's forearm.

Referring now to the drawings, the invention is shown generally at 10, including optional splint 18 in the preferred embodiment. The invention also includes a full-length sleeve 12 and elastic bands 14 and 16, one attached near each end of the sleeve as shown along A.

The sleeve 12 is sized to cover substantially the entire forearm from adjacent the elbow to adjacent the wrist of the user. The sleeve 12 is comprised of a center layer of neoprene 28 and inner and outer nylon layers 26 and 30 bonded to the neoprene. The neoprene preferred is supplied by Rubatex Corp. of Virginia, under stock number R-1400-N, or alternately R-5000. The inner layer is preferably plain nylon and the outer layer is preferably extra heavy-duty nylon for improved wear-resistance. However, these inner and outer layers may be any suitable flexible fabric to provide both skin comfort and added strength to the neoprene. The sleeve 12 is sized, in relation to the user's forearm, to be slightly smaller in circumference so as to provide forearm compression when stretched into the position shown in FIG. 1.

An import out aspect of the selection of neoprene as the center layer 28 of the sleeve 12, in addition to providing resiliency, is that of providing body heat insulation and retention. The warmth retained within the forearm and inner sleeve layer 28 serves to provide therapeutic warmth to promote healing and to keep muscles and connective tissue supple. This resiliency in the sleeve, supplemented by the inner and outer nylon layers 26 and 30, provides uniform forearm support to help prevent further injury.

Figure 2:
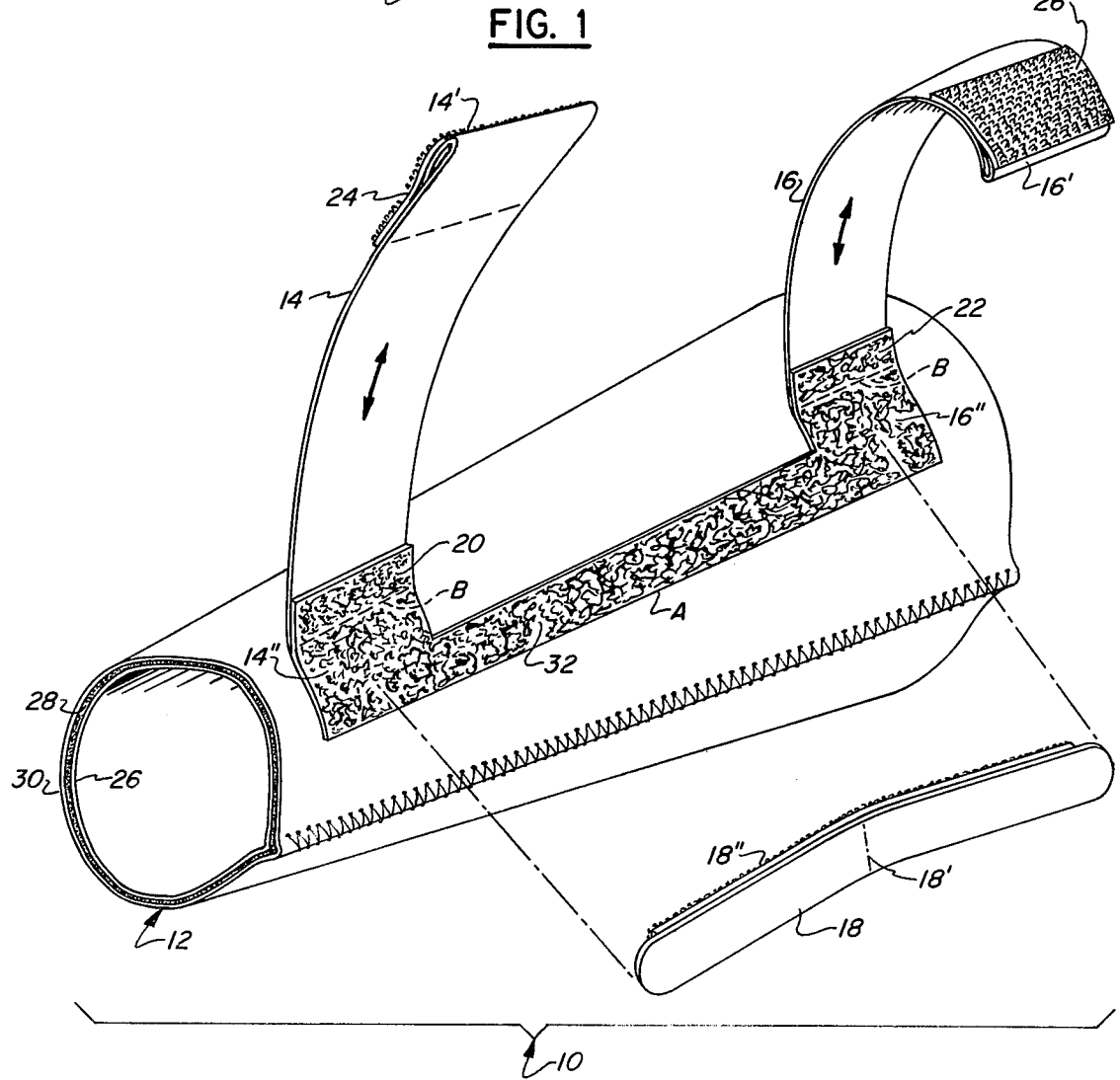
FIG. 2 is a perspective view of the invention, including optional splint.

After the resilient sleeve 12 has been stretched into position over the forearm, the elastic bands 14 and 16 stretchable and elastic in the direction of the arrows, may be wrapped around the sleeve and reattached to themselves by interconnectable Velcro portions 24 to 20 and 26 to 22. The amount that each elastic band is stretched as they are wrapped around the forearm and sleeve determines the additional compression and/or control placed upon the damaged underlying muscles. One end of each elastic band is attached to the sleeve substantially as shown for convenience in facilitating one-handed tightening and securing of each band into the above-described position around the sleeve and forearm. The preferred material for the elastic bands is a polyester elastic. The elastic bands 14 and 16 may be sewn, bonded, or the like to the sleeve. However, in the preferred embodiment, the mating Velcro portions 20 and 22 are integral with Velcro portion 32, forming a C-shape as shown in FIG. 2. The entire Velcro portion 32 is heat-bonded to the nylon outer sleeve layer 30 by compression and heating to approximately 380° with a heating iron. This amount of heat and pressure fuses the nylon layer 30 to the backing of Velcro portion 32. Preferably, said heat sealing occurs between edge line A and line B, leaving the remainder of the Velcro portions 20 and 22 free from the sleeve. One end of each elastic band 14 and 16 is preferably, prior to attaching Velcro portion 32 to the sleeve, heat bonded to the backing of a different free Velcro portion 20 or 22.

Should additional forearm stability and/or control be desired or additional compression be needed against the palm side of the forearm muscles between the elastic bands, a substantially rigid splint 18 may be fitted thereto, one end beneath each wrapped and secured elastic band. A slight bend 18' at or near the mid-point of the splint further increases the soothing, healing effect of this additional pressure and stability. In the preferred embodiment, interengaging fastening surfaces 18" and 32, e.g. Velcro, serve to retain the splint in place while the elastic bands are stretched and wrapped around the forearm and themselves secured in place. One portion 18" of the Velcro is adhered to the convex side of the splint while the other portion 32 of the Velcro, preferably integral with the Velcro portions 14" and 16" heat or adhesive bonded to the sleeve 12, matably secures the splint 18 along the sleeve 12.

A further function of the flexible bonds 14 and 16, particularly the flexible band 14 adjacent the user's wrist, is to help absorb shock loading into the user's arm protected by this invention caused by further tennis playing or any other activity resulting in strenuous forearm exertion.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An arm support for prevention and treatment of epicondylitis (tennis elbow) by providing muscle compression, stabilization, and heat retention for the forearm, said arm support comprising:

an elongated elastic sleeve having a center layer of neoprene rubber and inner and outer layers of flexible fabric;

said inner and outer layers each bonded to a different side by said neoprene rubber layer;

said sleeve shaped and sized to provide overall compression for the user's forearm muscles between just above the user's wrist to just below the user's elbow;

said neoprene rubber layer for retaining body heat beneath and within said neoprene rubber layer;

at least one elongated elastic pliable bands attached to said outer layer of said sleeve;

said bands including interengaging surfaces such that said bands may be stretched and secured about the user's forearm;

said bands for providing additional adjustable localized muscle compression.

2. An arm support as set forth in claim 1, further comprising:

an elongated substantially rigid splint;

said bands including at least two bands each attached at one end to said outer layer of said sleeve adjacent a different end of said sleeve;

said splint adapted to be removably installable between said bands, the ends of said splint fitting underneath said secured in place bands;

said spllint held securely along a portion of the length of the user's forearm for providing increased muscle compression therebeneath.

3. An arm support as set forth in claim 2, wherein:

said splint is curved at a mid-portion such that, when said splint is said installed, said curved mid-portion further compresses the forearm muscles therebeneath.

4. An arm support as set forth in claim 2, further comprising:

interengaging fastening surfaces between said splint and said outer layer of said sleeve.

5. An arm support as set forth in claim 4, wherein:

all said interengaging surfaces attached to said outer layer of said sleeve are an integral piece of Velcro;

said integral piece of Velcro having a backing side and an interengagable side;

at least a portion of said backing side of said integral piece of Velcro is heat sealed to said outer layer of said sleeve;

one end of each said elastic band is attached to said backing side of said integral piece of Velcro.

* * * * *